US012678079B2

(12) United States Patent
Bhandari et al.

(10) Patent No.: US 12,678,079 B2
(45) Date of Patent: Jul. 14, 2026

(54) METHOD AND SYSTEM FOR PERFORMING AUTOMATIC VESTIBULAR ASSESSMENT

(71) Applicant: FutureCure Health Pvt Ltd, Jaipur (IN)

(72) Inventors: Anita Bhandari, Jaipur (IN); Rajneesh Bhandari, Jaipur (IN)

(73) Assignee: FutureCure Health Pvt Ltd, Jaipur (IN)

( * ) Notice: Subject to any disclaimer, the term of this patent is extended or adjusted under 35 U.S.C. 154(b) by 495 days.

(21) Appl. No.: 16/856,958

(22) Filed: Apr. 23, 2020

(65) Prior Publication Data
US 2024/0197216 A1 Jun. 20, 2024

(30) Foreign Application Priority Data
May 24, 2019 (IN) .............................. 201911020680

(51) Int. Cl.
| | |
|---|---|
| *A61B 5/16* | (2006.01) |
| *A61B 3/14* | (2006.01) |
| *A61B 5/00* | (2006.01) |
| *G06T 7/00* | (2017.01) |
| *G06T 7/20* | (2017.01) |

(52) U.S. Cl.
CPC ................ *A61B 5/163* (2017.08); *A61B 3/14* (2013.01); *A61B 5/6803* (2013.01); *G06T 7/0012* (2013.01); *G06T 7/20* (2013.01); *G06T 2207/10048* (2013.01); *G06T 2207/20072* (2013.01); *G06T 2207/20081* (2013.01); *G06T 2207/30041* (2013.01)

(58) Field of Classification Search
CPC ......... A61B 5/163; A61B 3/14; A61B 5/6803; G06T 7/0012; G06T 7/20; G06T 2207/10048; G06T 2207/20072; G06T 2207/20081; G06T 2207/30041
See application file for complete search history.

(56) References Cited

U.S. PATENT DOCUMENTS

| | | | | |
|---|---|---|---|---|
| 2016/0166193 A1* | 6/2016 | Lin | ....................... | A61B 5/4023 |
| | | | | 600/301 |
| 2017/0258397 A1* | 9/2017 | Ghajar | ................... | A61B 3/085 |
| 2017/0323485 A1* | 11/2017 | Samec | .............. | A61B 5/14532 |
| 2018/0008141 A1* | 1/2018 | Krueger | .............. | A61B 5/7257 |
| 2018/0299953 A1* | 10/2018 | Selker | ................... | G06T 19/006 |
| 2020/0305707 A1* | 10/2020 | Fink | ..................... | A61B 3/0025 |

* cited by examiner

*Primary Examiner* — Sean A Frith
(74) *Attorney, Agent, or Firm* — Kunzler Needham Hilton

(57) ABSTRACT

The invention provides a headgear apparatus for performing vestibular assessment of a user. The headgear apparatus includes a processor, a memory and a display device for displaying a plurality of visual stimuli and a hardware means to provide a plurality of non-visual stimuli to the user. A plurality of infrared cameras and an inertial measurement device are employed for measuring eye movement and head movement in response to visual stimuli/non-visual stimuli provided to the user and generating one or more graph based patterns. Headgear apparatus further includes a laser source for providing a laser beam to be projected on a surface during presentation of non-visual stimuli. Accordingly, a machine learning model is employed for interpreting the one or more graph based patterns to detect the presence of an abnormality.

14 Claims, 14 Drawing Sheets

100

| Type | Left Cycle Right Eye | Left Cycle Left Eye | Right Cycle Right Eye | Right Cycle Left Eye |
|---|---|---|---|---|
| Target Movement | 7 | 7 | 7 | 7 |
| Accepted Saccades | 6 | 6 | 6 | 6 |
| Latency(Millisecond) | 318 | 345 | 347 | 335 |
| Velocity(deg/sec) | 288 | 267 | 285 | 254 |
| Precision(%) | 79 | 83 | 74 | 63 |

| Test | Right Eye SPV (/sec) | Right Eye Beats/10 sec | Left Eye SPV (/sec) | Left Eye Beats/10 sec |
|---|---|---|---|---|
| Left Horizontal | 0 | 0 | 0 | 0 |
| Left Vertical | 0 | 0 | 0 | 0 |
| Right Horizontal | 0 | 0 | 0 | 0 |
| Right Vertical | 0 | 0 | 0 | 0 |

| Test | Right Eye SPV (/sec) | Right Eye Beats/30 sec | Left Eye SPV (/sec) | Left Eye Beats/30 sec |
|---|---|---|---|---|
| Up Horizontal | 0 | 0 | 0 | 0 |
| Up Vertical | 0 | 0 | 0 | 0 |
| Down Horizontal | 0 | 0 | 0 | 0 |
| Down Vertical | 0 | 0 | 0 | 0 |

METHOD AND SYSTEM FOR PERFORMING AUTOMATIC VESTIBULAR ASSESSMENT

CROSS-REFERENCE TO RELATED APPLICATION

This application claims the benefit of Indian Patent Application No. 201911020680, filed on May 24, 2019, entitled "METHOD AND SYSTEM FOR PERFORMING AUTOMATIC VESTIBULAR ASSESSMENT", which application is incorporated herein by reference in its entirety and for all purposes.

FIELD OF THE INVENTION

The invention generally relates to vestibular assessment by evaluating oculomotor measurements. More specifically, the invention relates to employing a headgear apparatus for performing vestibular assessment, further enabling automatic interpretation of one or more vestibular conditions.

BACKGROUND OF THE INVENTION

Videonystagmography (VNG) is a technology for testing inner ear and central motor functions, a process known as vestibular assessment, wherein infrared cameras are primarily employed to trace eye movements during visual stimulation and positional changes.

Traditionally employed VNG systems include tracking of only an eye movement of a user of the googles with infrared, wherein a head movement of the user while undergoing one or more vestibular tests is not accounted for, thereby leading to erroneous results. Further, the erroneous results are forwarded to a physician/doctor for interpretation, eventually leading to an incorrect diagnosis. The vestibular assessment is thus dependent only on measurement of eye movement of the user, while more than one sensory input will provide a comprehensive measurement of the user's vestibular condition.

The results of sensory inputs/stimuli are often converted into graph based patterns to be interpreted by doctors/physicians and eventually arrive at a diagnosis with respect to the condition of the user. However, in the existing scenario, even highly trained doctors/physicians are unable to interpret the complex graph based patterns leading to erroneous diagnosis.

Traditionally employed methods of videonystagmography, also project one or more visual stimuli of vestibular tests by projecting images on a screen using a light-emitting diode (LED) projector or a light bar consisting of a series of LEDs. Furthermore, while positional testing includes head and torso movement as non-visual stimuli, simultaneous tracking of the eye movement along with head and torso movement is currently unavailable. Videonystagmography systems providing real life projections as stimuli including visual as well as non-visual stimuli are also unavailable.

Therefore, in light of the above, there exists a need for a method and system for enabling an automated vestibular assessment for interpreting a vestibular condition associated with a user and employing a compact and portable system providing a comprehensive and error free measurement by accounting for more than one sensory input.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the invention.

FIGS. 4A and 4B illustrate graph based patterns of horizontal smooth pursuit visual stimuli, wherein FIG. 4A is indicative of recorded eye movement in the horizontal axis for a normal user and FIG. 4B is indicative of recorded eye movement showing abnormal horizontal pursuit, more specifically a condition of mTBI (mild Traumatic Brain Injury).

Figure 1:
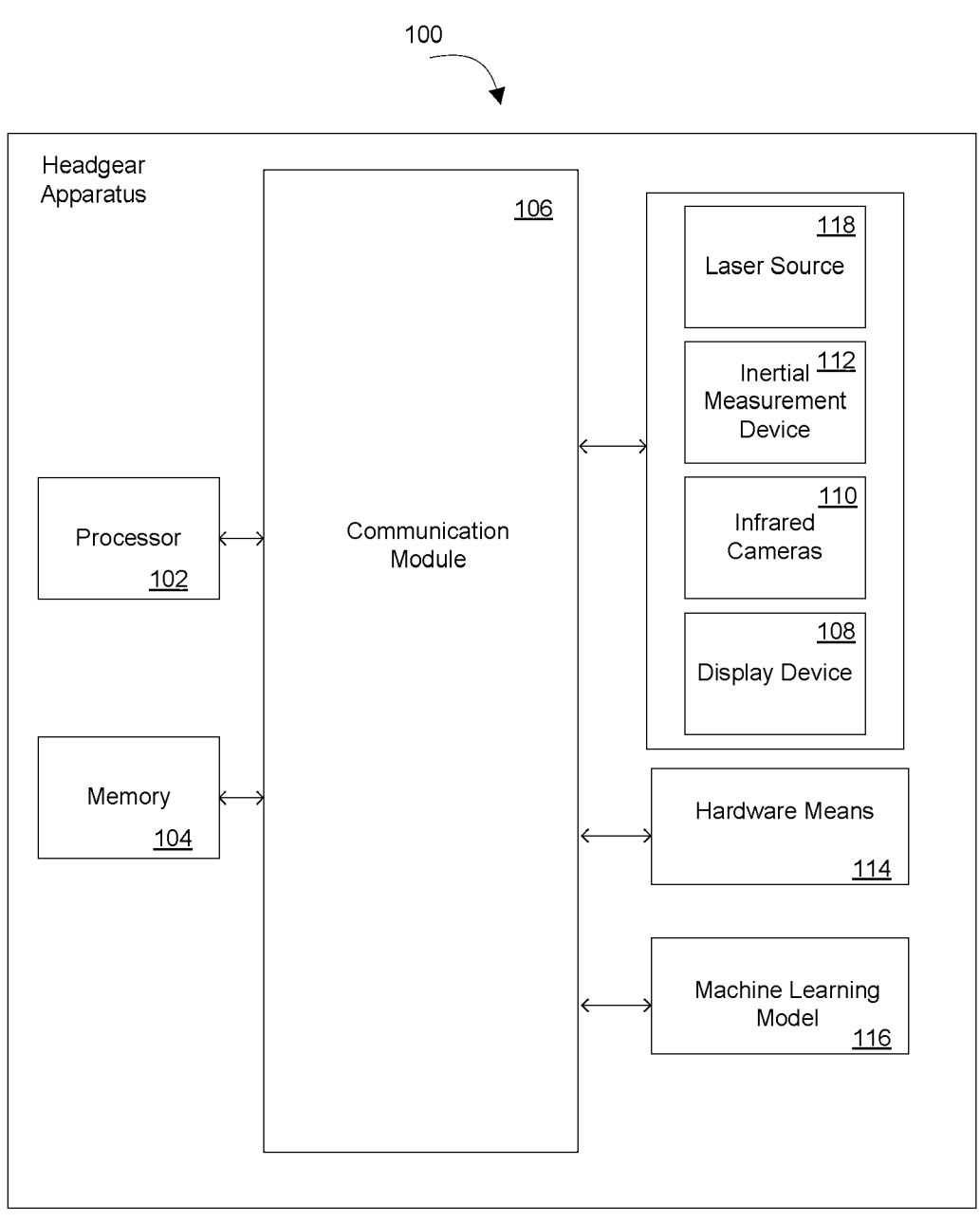
FIG. 1 illustrates a headgear apparatus for performing vestibular assessment in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of method steps and system components related to a headgear apparatus for performing vestibular assessment of a user by employing a machine learning model for assessing an eye movement and head movement of the user, leading to automatic interpretation of a vestibular condition associated with the user.

Accordingly, the system components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article or composition that comprises a list of elements does not include only those elements but may include other elements not expressly listed or inherent to such process, method, article or composition. An element proceeded by "comprises . . . a" does not, without more constraints, preclude the existence of additional identical elements in the process, method, article or composition that comprises the element.

Various embodiments of the invention provide a headgear apparatus for enabling a vestibular assessment of a user by employing a machine learning model. The headgear apparatus includes a memory and a processor communicatively coupled to the memory. The headgear apparatus includes a display device for providing a plurality of visual stimuli to the user, and a plurality of sensors for measuring a sensory output from the user in response to the visual stimuli provided by the display device. The sensory outputs include one or more of an eye movement measured by a plurality of infrared cameras and a head movement measured by an inertial measurement device. Further, the headgear apparatus also includes a hardware means for providing a plurality of non-visual stimuli to measure a response to the non-visual stimuli. Accordingly, one or more measurements including sensory outputs of the user are employed to generate one or more graph based patterns for automatic interpretation of the presence of an abnormality by using a machine learning model.

FIG. 1 illustrates a headgear apparatus 100 for performing vestibular assessment of a user in accordance with an embodiment of the invention.

As illustrated in FIG. 1, headgear apparatus 100 includes a processor 102 and a memory 104 communicatively coupled to processor 102. Processor 102 and memory 104 further communicate with one or more components via a communication module 106. Communication module 106 may be configured to transmit data between modules, engines, databases, memories, and other components of headgear apparatus 100 for use in performing the functions discussed herein. Communication module 106 may include one or more communication types and utilize various communication methods for communication within headgear apparatus 100.

Headgear apparatus 100 is worn by a user undergoing vestibular assessment. Headgear apparatus 100 further includes a display device 108 communicatively coupled to processor 102 and memory 104.

Headgear apparatus 100 further includes a plurality of infrared cameras 110 for measuring an eye movement of the user, an inertial measurement device 112 for measuring a head movement of the user and a laser source 118. Display device 108 is configured to provide a plurality of visual stimuli to the user undergoing vestibular assessment. Plurality of infrared cameras 110 and inertial measurement device 112 are employed for measuring an eye movement and a head movement of the user in response to the plurality of visual stimuli provided by display device 108. Laser source 118 provides a laser beam to be projected on a surface during presentation of non-visual stimuli. Headgear apparatus 100 further includes a hardware means 114 for providing a plurality of non-visual stimuli to the user.

Processor 102 is configured to generate one or more graph based patterns based on one of an eye movement measured by plurality of infrared cameras 110 and head movement measured by inertial measurement device 112. Processor 102 further generates one or more graph based patterns and employs a machine learning model 116 for detecting a presence of an abnormality associated with a graph based pattern generated from the one or more eye movements and head movements. The presence of an abnormality is determined based on one or more patterns, including, but not limited to, a nystagmus pattern, eye movement pattern, head movement pattern and torsion pattern. The determined abnormality is automatically interpreted by the method and system in connection with a vestibular condition of the user. One or more vestibular conditions diagnosed during a vestibular assessment include, but are not limited to, brain diseases, tumors, nerve palsy, concussion, Attention-deficit/hyperactivity disorder (ADHD), strokes, early Parkinson's, Multiple Sclerosis and Benign Paroxysmal Positional Vertigo (BPPV).

The plurality of visual stimuli provided on display device 108 of headgear apparatus 100 correspond to the following tests including, but not limited to, a smooth pursuit test, saccadic test, optokinetic test, gaze test and a combination.

The plurality of non-visual stimuli provided by hardware means 114 include, but are not limited to, mastoid vibration, caloric, Valsalva, Hyperventilation, Vestibulo-Ocular Reflex ( ) suppression, VOR, head shaking, head thrust and head impulse.

The plurality of non-visual stimuli provided by hardware means 114 may further include positional tests, such as, but not limited to, DixHall Pike, Supine and deep head hanging.

Inertial measurement device 112 measures one of a deliberate head movement and an erroneous head movement, thereby enabling processor 102 to differentiate between a deliberate head movement and an erroneous head movement.

In an embodiment, headgear apparatus 100 is a pair of augmented reality goggles. Headgear apparatus 100 can also be a pair of virtual reality goggles. The pair of augmented reality goggles are employed for performing vestibular measurement on a user.

Figure 2:
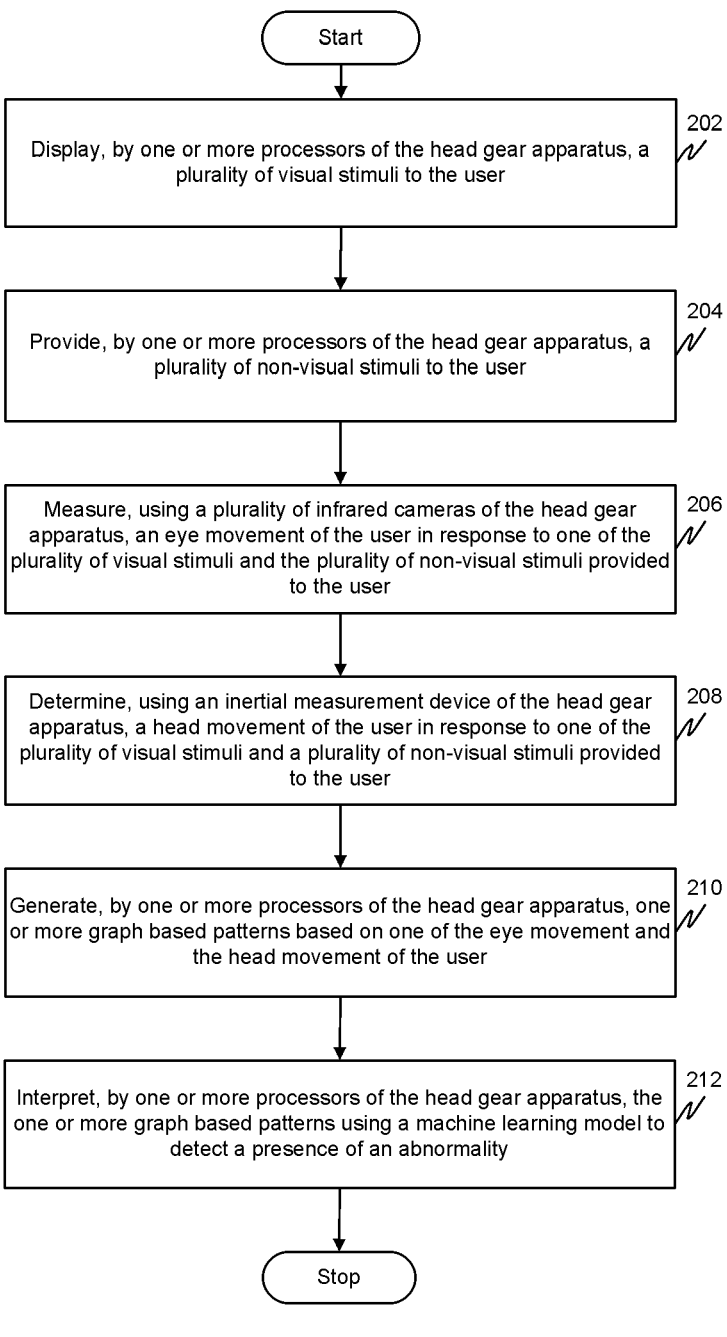
FIG. 2 illustrates a flowchart of a method for performing vestibular assessment using a headgear apparatus in accordance with an embodiment of the invention.

FIG. 2 is illustrative of flowchart of a method for performing vestibular assessment using headgear apparatus 100 in accordance with an embodiment of the invention.

Referring to FIG. 2, at step 202, a plurality of visual stimuli is provided to the user undergoing vestibular assessment via display device 108. In a next step 204, one or more processors, provides a plurality of non-visual stimuli to the user.

After providing visual as well as non-visual stimuli to the user, a subsequent step 206 includes measuring an eye movement of the user in response to the plurality of visual stimuli provided to the user on display device 108, the measurement of eye movement performed by plurality of infrared cameras 110. In an ensuing step 208, inertial measurement device 112 is employed to determine a head movement of the user in response to one of the plurality of visual stimuli as well as non-visual stimuli provided to user. In accordance with the method, inertial measurement device 112 measures one of a deliberate head movement and an erroneous head movement, thereby enabling processor 102 to differentiate between a deliberate head movement and an erroneous head movement.

At step 210, one or more processors of the headgear apparatus 100 are configured to generate graph based patterns based on one of the eye movement and the head movement of the user, measured by plurality of infrared cameras 110 and inertial measurement device 112 respectively.

Moving on, at step 212, a machine learning model 116 is employed by one or more processors of the headgear apparatus 100 to interpret one or more graph based patterns to detect a presence of an abnormality, the abnormality based on one of a nystagmus pattern, eye movement pattern, head movement pattern and torsion pattern.

The machine learning model 116 employs Deep Neural Networks (DNNs) and more specifically Convolutional Neural Networks (CNNs) for performing vestibular assessment of a user by identifying one or more graph-based patterns associated with one of a nystagmus pattern, eye movement pattern, head movement pattern and torsion pattern, in accordance with training models. Further, interpretation of the identified graph-based patterns is performed by employing one or more image processing techniques based on one or more curves and prediction of data points.

In an embodiment, in accordance with the method and system, a plurality of visual stimuli corresponding to one or more tests, the one or more tests including, but not limited to, smooth pursuit, saccade test, optokinetic test, gaze test and a combination, are provided. More specifically, the one or more tests include at least one of horizontal/vertical smooth pursuit test, asymmetrical smooth pursuit test, reduced smooth pursuit and reversed smooth pursuit. The one or more tests may further include at least one of horizontal saccades test and a vertical saccades test.

Accordingly, the method and system by virtue of headgear apparatus 100, generates graph-based patterns specific to eye movements measured by plurality of infrared cameras 110, in response to the plurality of visual stimuli provided on display device 108.

Figure 3:
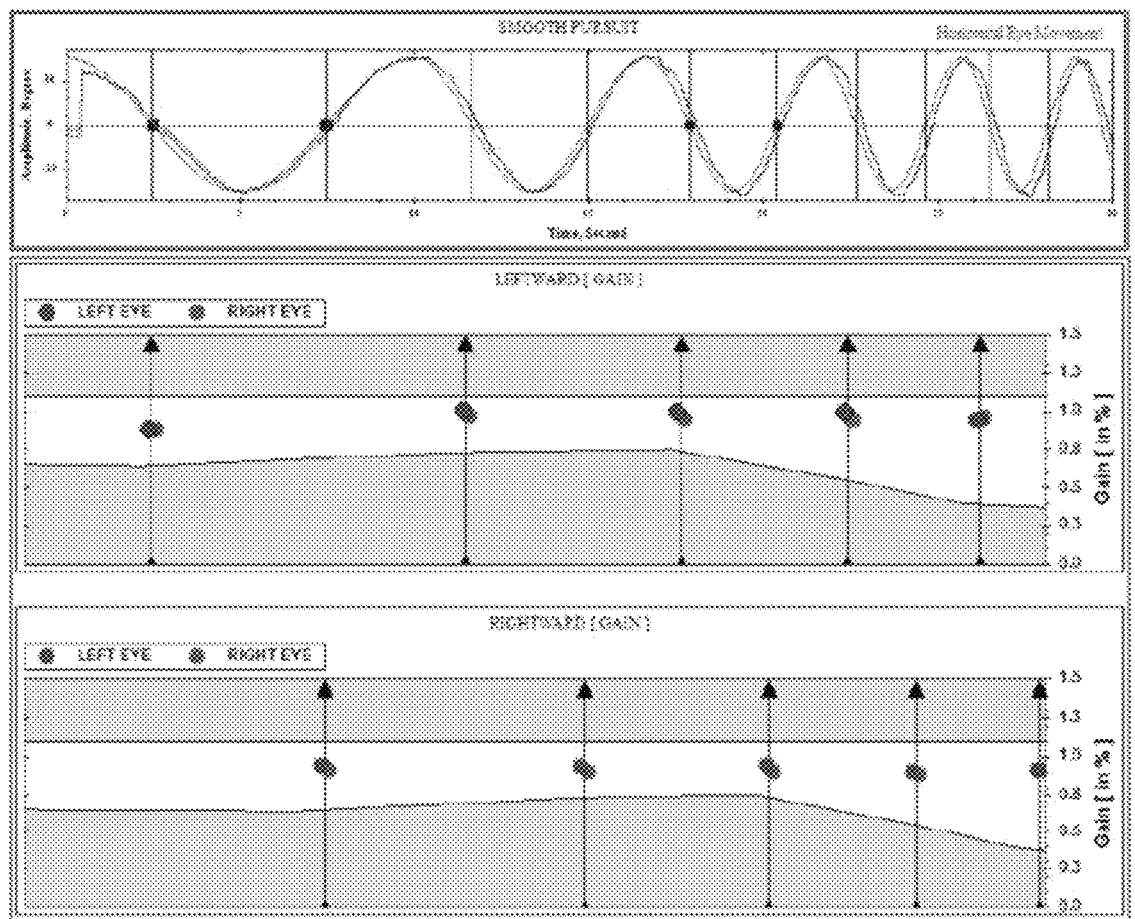
FIG. 3 illustrates a graph based pattern of smooth pursuit visual stimulus while following a target with increasing velocity in a normal user based on pursuit gain in left and right directions for the left eye and right eye.

In a smooth pursuit test, the ability of a user's eye to follow a target across the visual field of the fovea, thereby preventing a retinal slip, is tested. FIG. 3 is illustrative of a graph based pattern of smooth pursuit visual stimulus while following a target with increasing velocity/frequency in a normal user based on pursuit gain in left and right directions for the left eye and right eye. A normal eye movement will be able to follow the target smoothly. Further, velocity gain/pursuit gain is measured to the right and the left, wherein the pursuit gain is a ratio of the eye velocity to the target velocity. In users with symmetrical pursuits, the users are classified in accordance with pursuit gains.

Figure 4A:
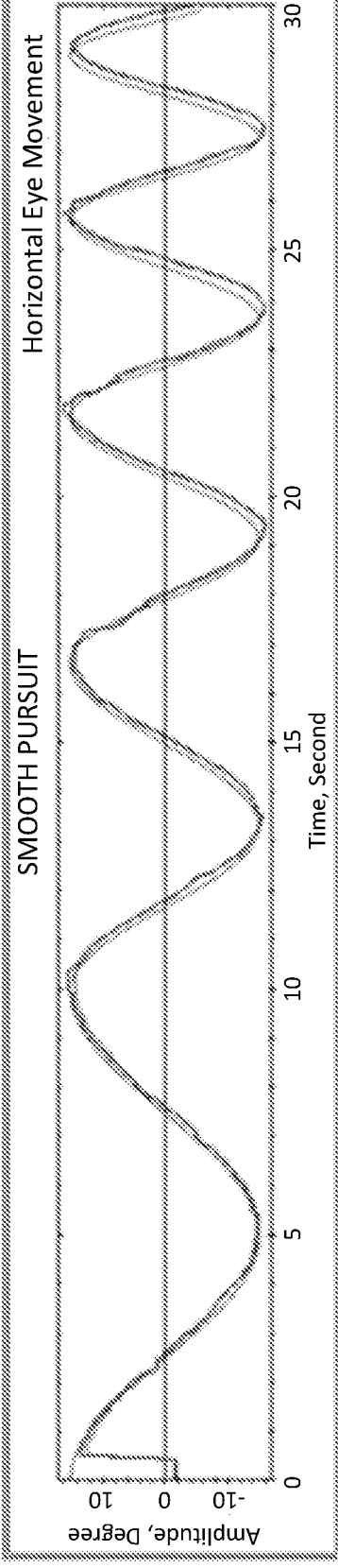
Figure 4B:
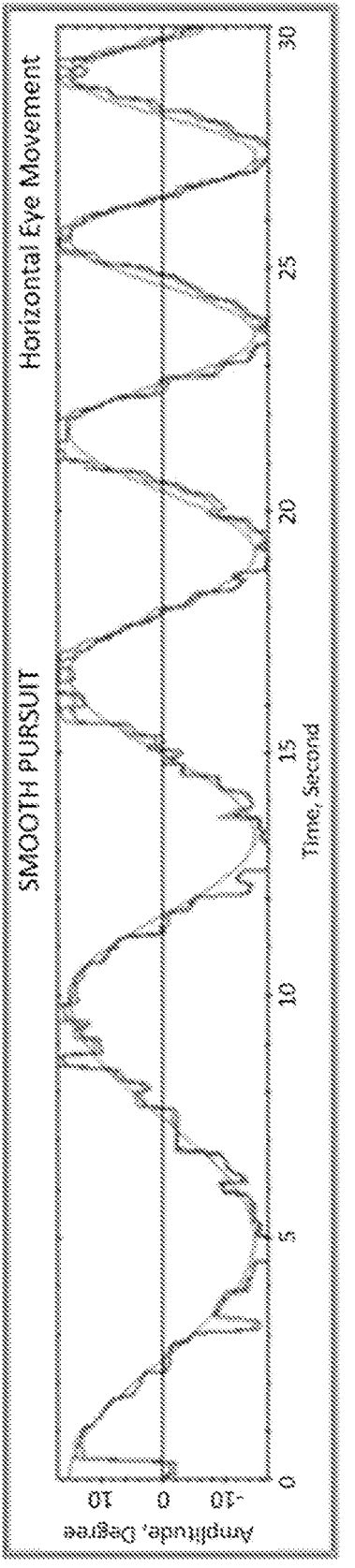

In the horizontal smooth pursuit test, the user is directed to follow a target moving across display device 108 of headgear apparatus 100 along the horizontal axis in both directions for measuring movement of a left eye and a right eye of the user. With respect to the horizontal smooth pursuit test, velocity gain asymmetry is a difference between the pursuit gain to the right and left. The method and system accordingly interprets graph based patterns in response to the horizontal smooth pursuit test, wherein the user has poor peripheral vision but good central vision leading to a tunnel vision. In an example, referring to FIGS. 4A and 4B, left and right movements indicated by blue and red respectively are illustrated, wherein FIG. 4A is indicative of recorded eye movement in the horizontal axis for a normal user and FIG. 4B is indicative of recorded eye movement showing abnormal horizontal pursuit. The method and system interprets the abnormal horizontal pursuit for identifying the user having a condition of mTBI (Mild Traumatic Brain Injury).

An abnormal horizontal smooth pursuit may include an asymmetrical pursuit, wherein the graph-based patterns of the asymmetrical pursuit includes a pursuit gain significantly increased in one direction with respect to mean gain and standard deviation in each direction. The graph-based patterns are generated by the method and system and interpreted by using a machine learning model 116. Subsequently, the interpretation is based on a comparison with a pursuit stimulus having constant velocity in terms of rightward and leftward gain.

Figure 5:
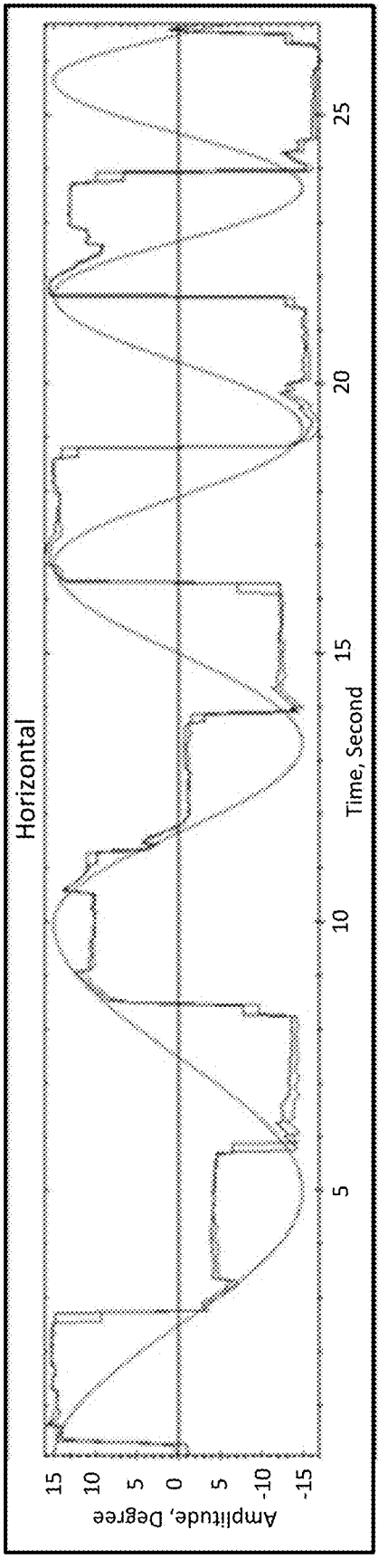
FIG. 5 is illustrative of a graph-based pattern including square wave jerks during smooth pursuit.

Another abnormal smooth pursuit may include a reduced smooth pursuit, wherein the left and right eye movement follow a smooth pursuit along with extraneous saccades in the form of square wave jerks. FIG. 5 is illustrative of a graph-based pattern including square wave jerks during smooth pursuit, wherein the larger deviations are the saccades and superimposed block like deviations are square wave jerks.

Figure 6:
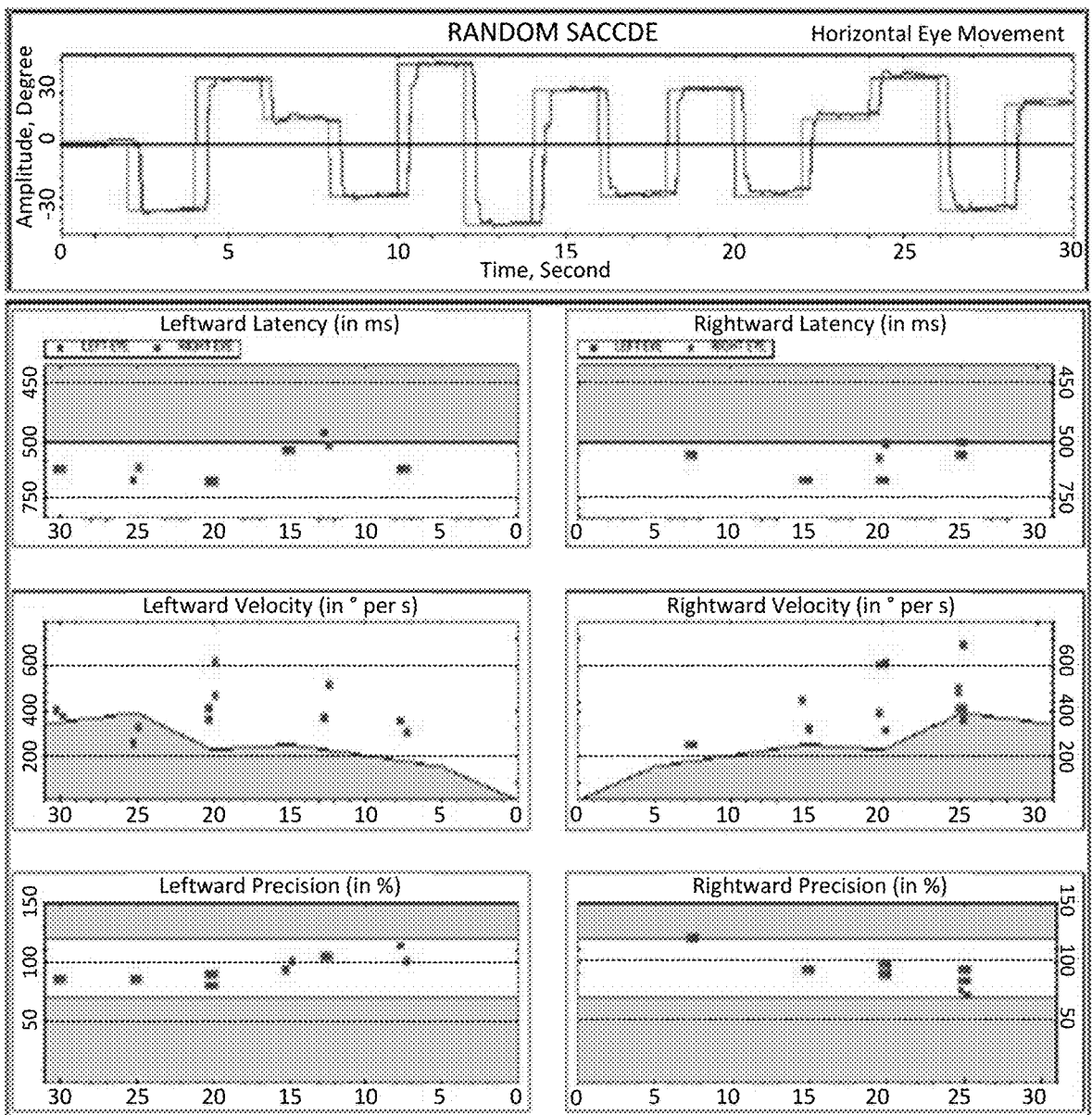
FIG. 6 is illustrative of a graph-based pattern of a normal user with an ability to undergo a saccade test, wherein the left and right eye movement produce a tracing (indicated in blue & red) identical to the stimulus (indicated in green).

In a visual stimulus provided for a saccade test, a user's ability to retain images of one or more objects in a scene within the periphery of the visual field on the fovea, thereby preventing retinal slip, is tested. FIG. 6 is illustrative of a normal user with an ability to undergo a saccade test, wherein the left and right eye movement produce a tracing (indicated in red) identical to the stimulus (indicated in green). Accordingly, a latency of the saccade is measured, wherein the latency is the delay between an onset of a target movement and initiation of eye movement towards a new target position. The method and system considers a consistent latency of above 260 to 270 milliseconds to be abnormal. Further, accuracy and velocity are parameters considered by the method and system, along with latency, during a visual stimulus such as the saccade test. Accuracy is the amplitude of the eye movement relative to the target, wherein up to 10-15% hypometria and 15-20% hypermetria is considered normal for a user. Velocity is the time taken to complete a saccade once initiated, wherein less than 430 deg/sec is optimum for a large amplitude and less than 200 deg/sec is considered optimum for a small amplitude.

Figure 7:
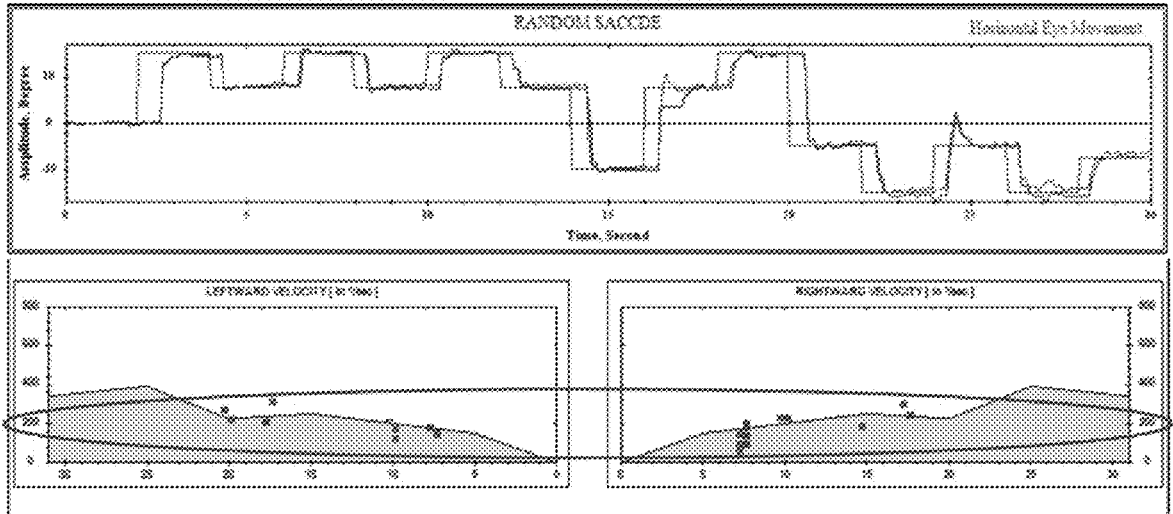
FIG. 7 is illustrative of a graph-based pattern of a user presented with saccades and the saccades showing abnormal velocities.

FIG. 7 is illustrative of a graph-based pattern indicative of a saccade with abnormal velocity. Referring to FIG. 7, saccadic velocity may be too slow, too fast or have substantially different velocities in one eye or direction with respect to the other.

Figure 8:
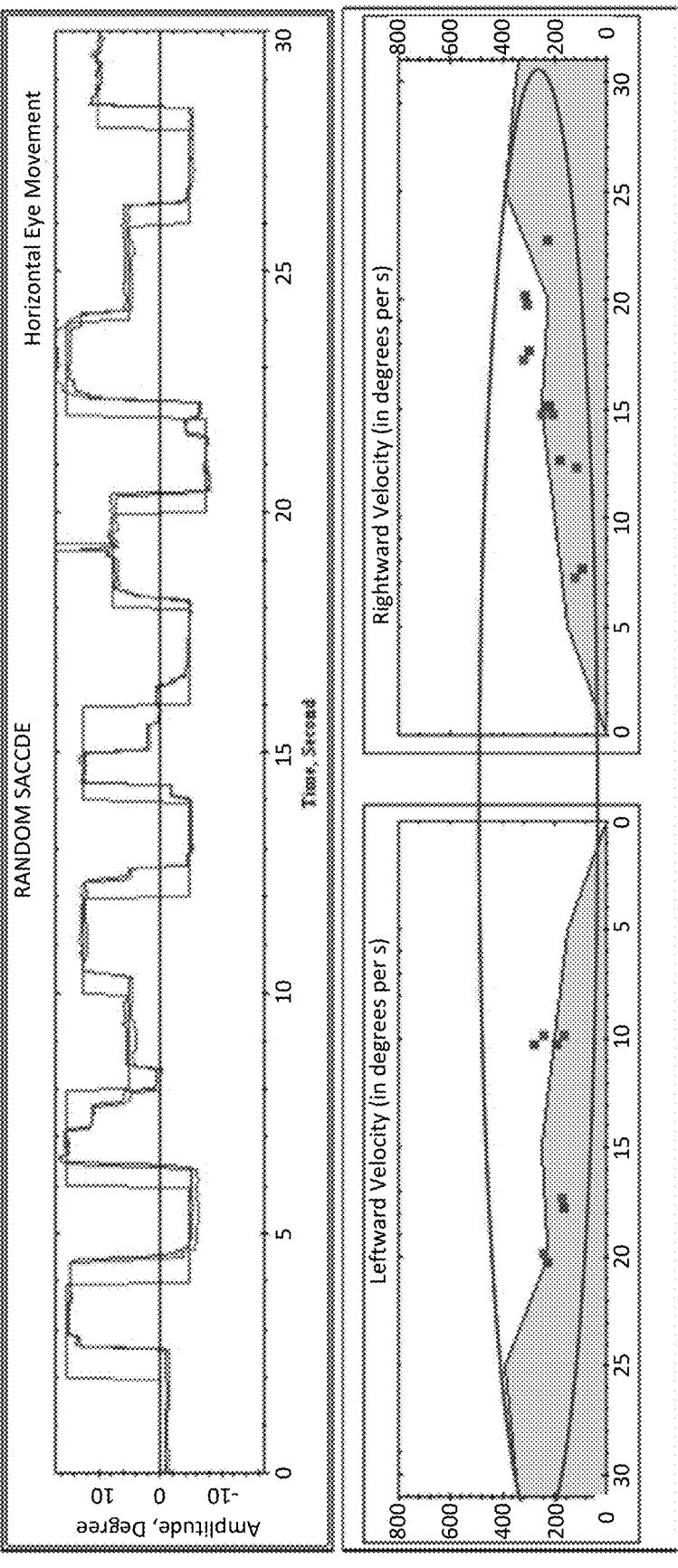
FIG. 8 is illustrative of a graph-based pattern indicating saccadic slowing.

More specifically, saccadic slowing is when mean saccadic velocity for a particular amplitude is slower than the lower fifth percentile of normal. FIG. 8 is illustrative of graph-based pattern indicating saccadic slowing.

Figure 9:
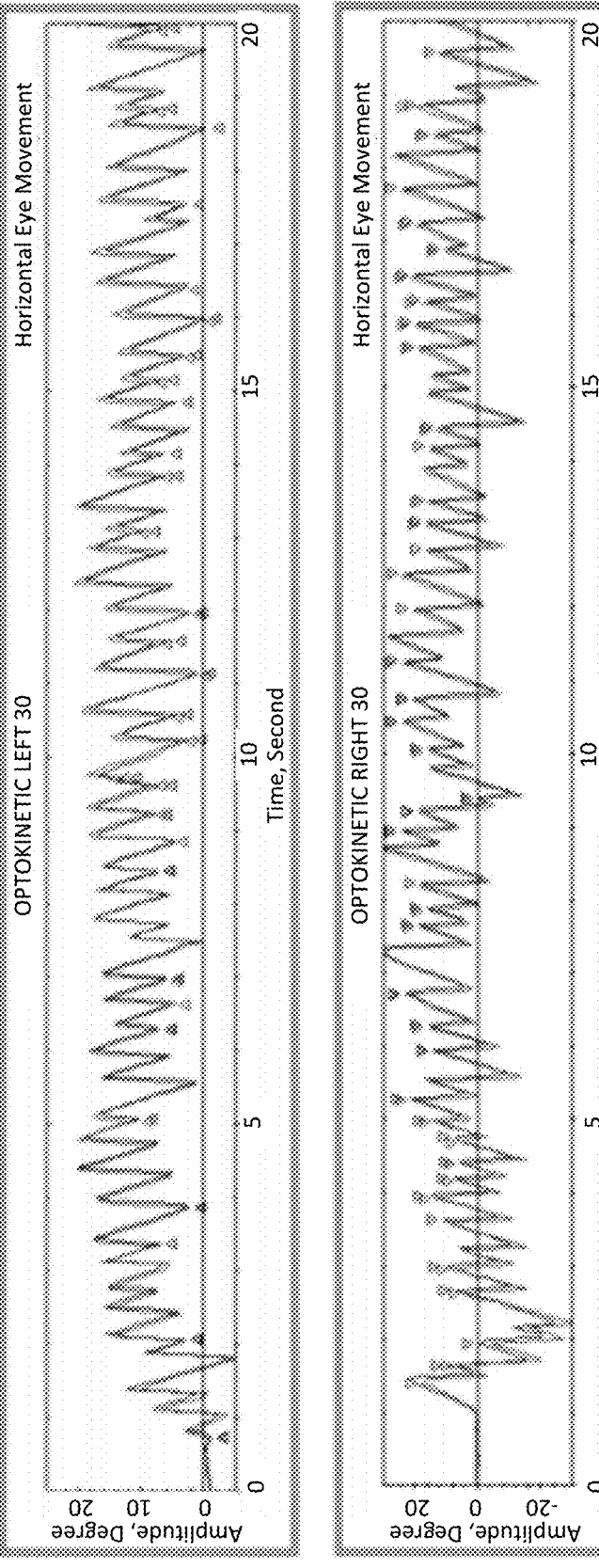
FIG. 9 is illustrative of a graph-based pattern of a normal user evaluating an optokinetic nystagmus.

In a visual stimulus provided for the optokinetic test, a user's ability to follow multiple moving objects on the fovea, thereby preventing a retinal slip, is tested. The optokinetic test employs both foveal and extrafoveal vision. Optokinetic nystagmus is the eye movement following a moving field instead of a single target. FIG. 9 is illustrative of a graph-based pattern of a normal user, similar or slightly greater than a smooth pursuit gain. Optokinetic nystagmus is evaluated by comparing one or more values with the values of smooth pursuit. A user undergoing an optokinetic test adopts an eye position opposite to the velocity of the optokinetic moving field produced, known as shift of the beating field. One or more abnormalities determined based on optokinetic nystagmus movements associated with one or more vestibular conditions include symmetrically reduced optokinetic gain, asymmetrical optokinetic gain and reversed optokinetic.

Figure 10A:
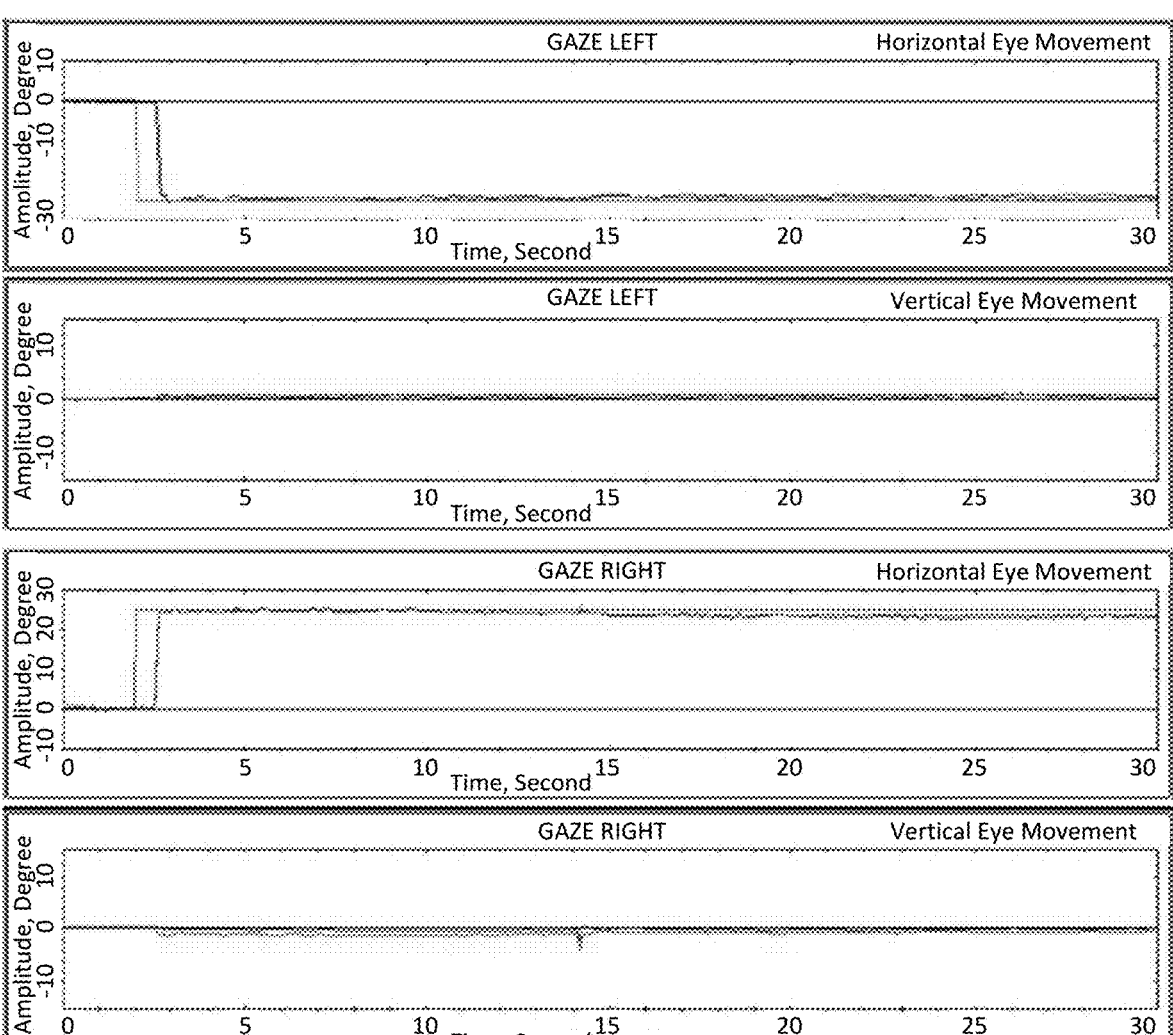
FIG. 10A is illustrative of a graph-based pattern of a left and right gaze-evoked test showing an absence of a nystagmus.
Figure 10B:
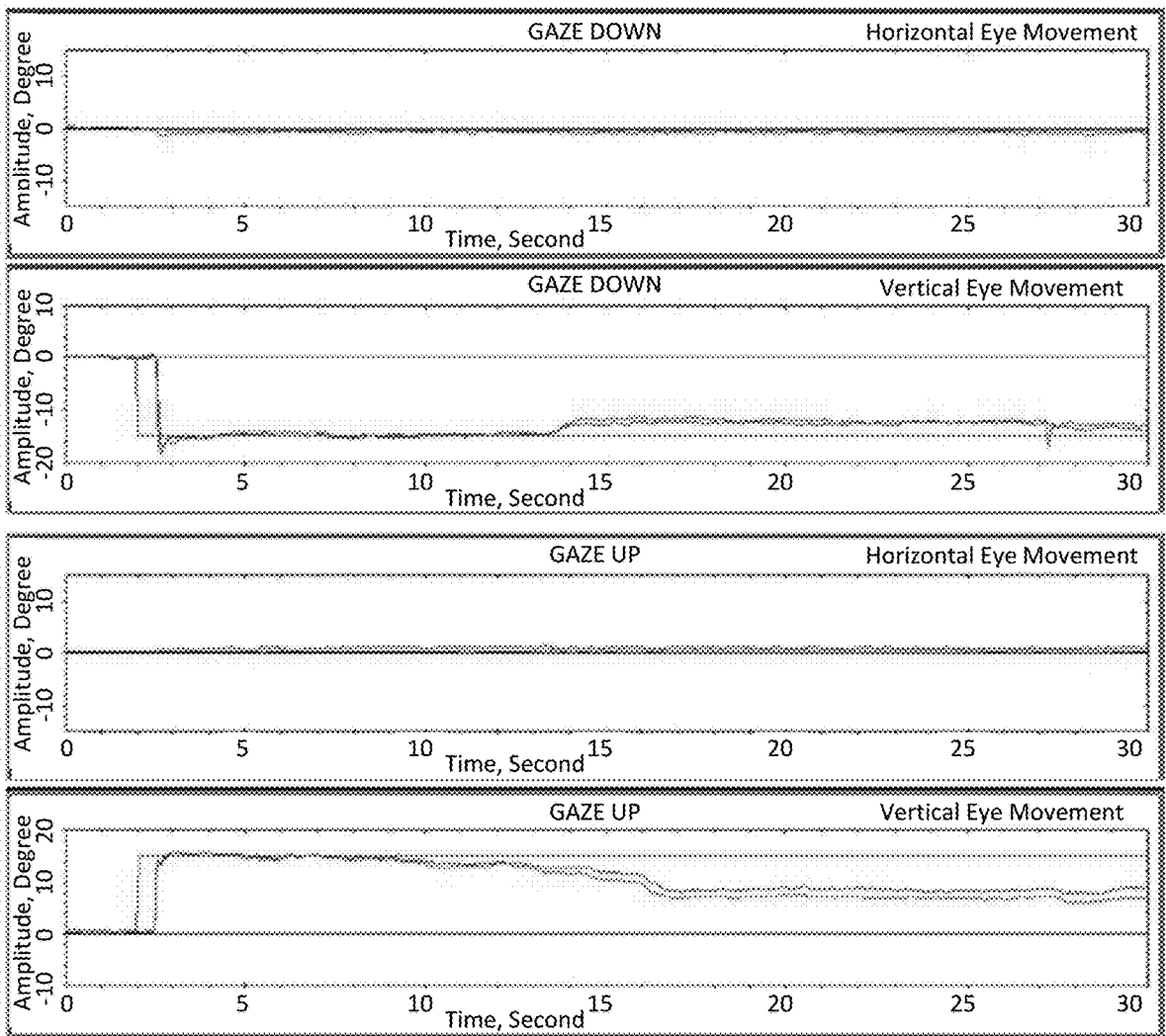
FIG. 10B is illustrative of a graph-based pattern of an up and down gaze test showing no nystagmus.

In a visual stimulus provided for a gaze-evoked nystagmus, a user is directed to look in a particular direction, wherein drift of the eye is present only in certain directions of gaze away from straight ahead. In a gaze test, the user is directed to look left and right at angles of 25 degrees and up and down at angles of 15 degrees and fixate for at least 20 seconds and accordingly a nystagmus is recorded. FIG. 10A is illustrative of a graph-based pattern of a left and right gaze-evoked test showing an absence of a nystagmus. FIG. 10B is illustrative of a graph-based pattern of an up and down gaze test showing no nystagmus.

Figure 11A:
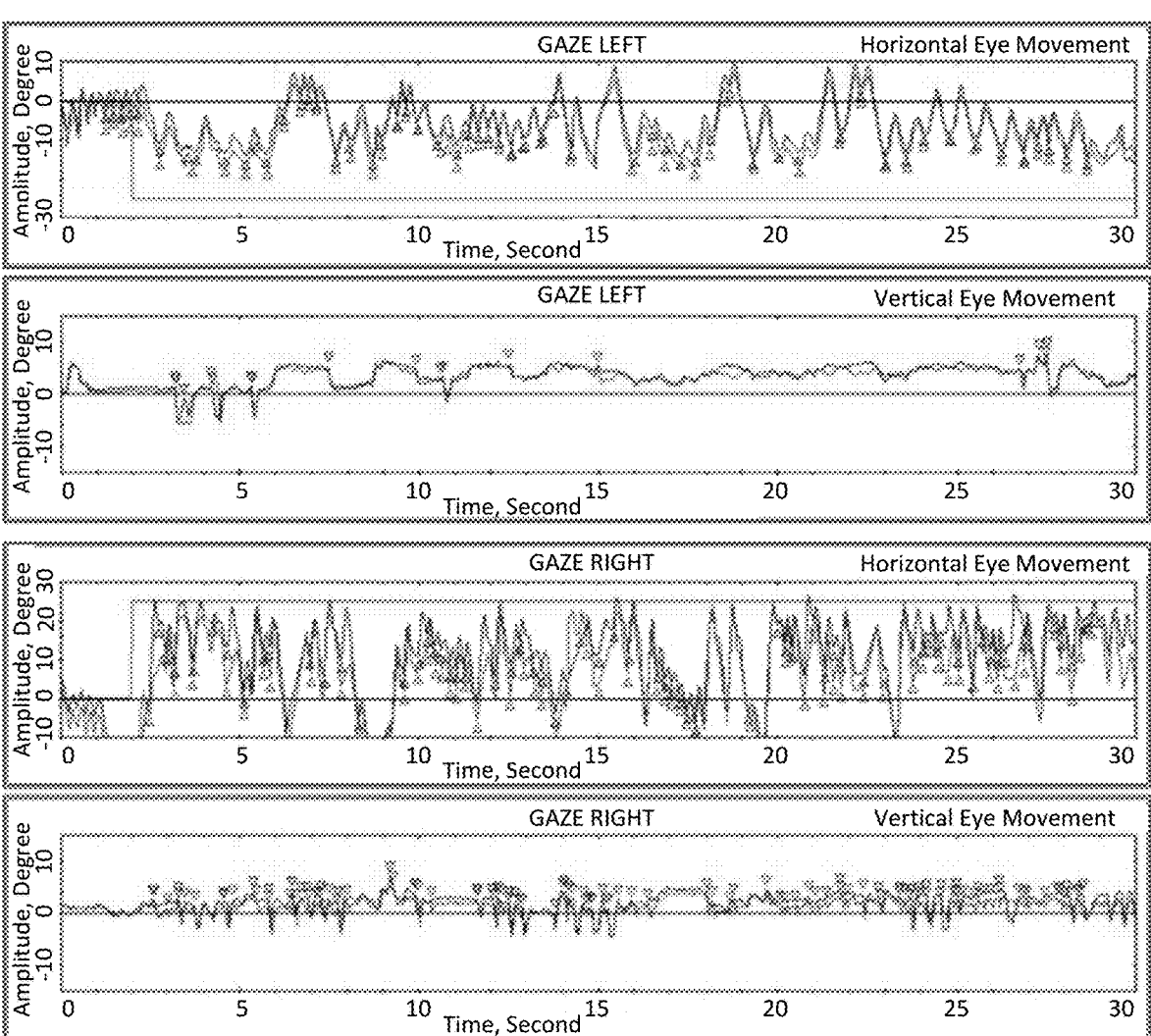
FIG. 11A is illustrative of a graph-based pattern of a left and right gaze test showing nystagmus.
Figure 11B:
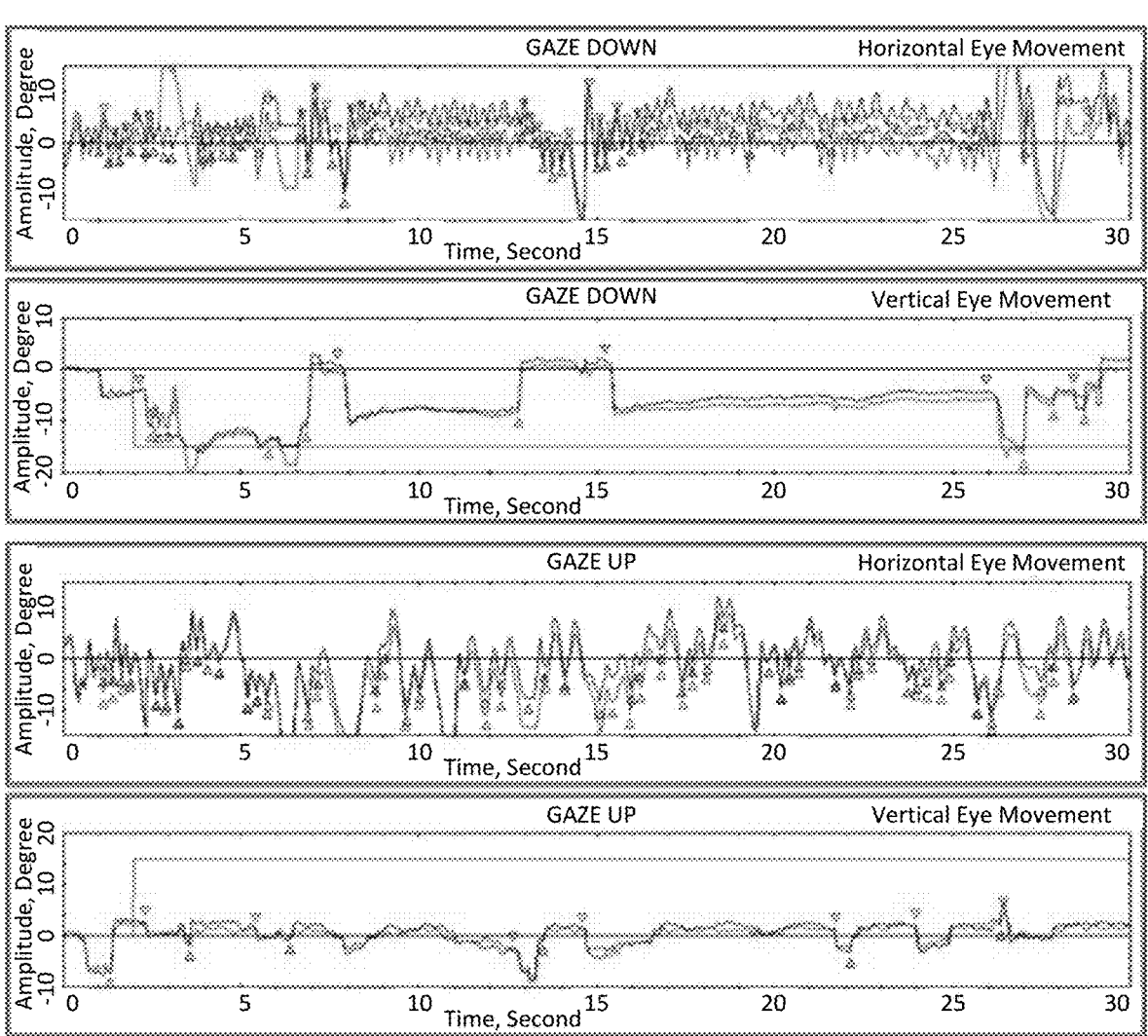
FIG. 11B is illustrative of a graph-based pattern of an up and down gaze test showing nystagmus.

A gaze-evoked nystagmus includes a horizontal gaze-evoked nystagmus and a vertical gaze-evoked nystagmus. In a horizontal gaze-evoked nystagmus, a nystagmus is present with fixation, wherein the intensity does not increase significantly. Similarly, a nystagmus is present without fixation, wherein the intensity is less than a threshold of the normal test. One or more abnormalities in the gaze-evoked nystagmus test includes square wave jerk nystagmus and ocular flutter among other abnormalities. FIG. 11A is illustrative of a graph-based pattern of a left and right gaze test showing nystagmus. FIG. 11B is illustrative of a graph-based pattern of an up and down gaze test showing nystagmus.

In accordance with the method and system, a plurality of non-visual stimuli are also provided to the user, the plurality of non-visual stimuli, including but not limited to, mastoid vibration, caloric, Valsalva, Hyperventilation, Vestibulo-Ocular Reflex (VOR) suppression, VOR, head shaking, head thrust and head impulse.

In a non-visual stimulus such as a Valsalva maneuver, pressure sensitivity of the user is measured by straining a user's ear to increase pressure in the middle ear, eventually transmitted to the inner ear. Accordingly, nystagmus and torsional patterns in response to the Valsalva maneuver are recorded. In a non-visual stimulus such as a VOR suppression, eye movement as well as head movement is measured as a user follows a head fixated laser point as the user's head is moved. The fixated laser point is by virtue of a laser beam from laser source 118 of headgear apparatus 100, to enable measurement of user's head movement and eye movement along the head fixated laser point projected on a wall.

Figure 12:
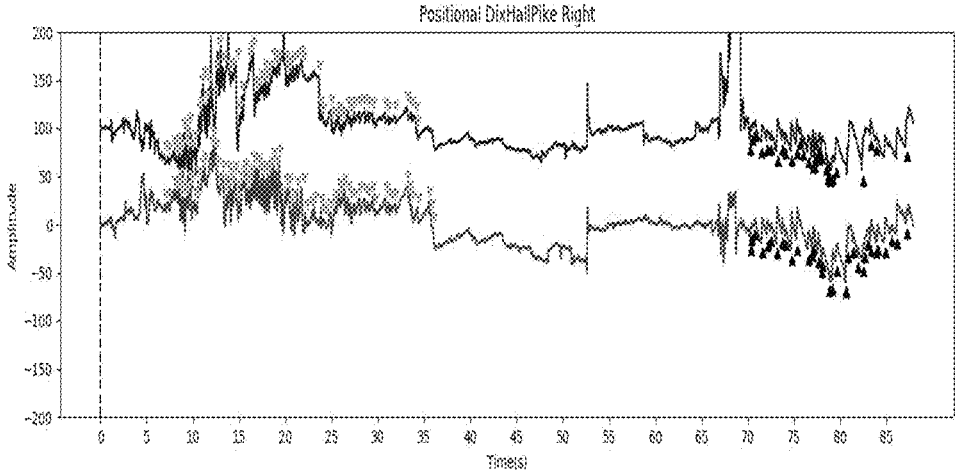
FIG. 12 is illustrative of a graph-based pattern of torsion as measured in a positional test of Dixhall pike.

Further, positional tests such as Dixhall pike are provided to the user as a part of a non-visual stimuli, wherein a user's head is turned 45 degrees to stimulate posterior semicircular canal and position of the otoliths in the posterior semicircular canal is determined. Accordingly, head position/movement is tracked using inertial measurement devices and eye movement is tracked by the plurality of infrared cameras. The method and system records the different positions in terms of nystagmus and torsion patterns. FIG. 12 is illustrative of a graph-based pattern of torsion as measured in a positional test of Dixhall pike. One or more parameters associated with the nystagmus and torsion patterns determined also include slow phase velocity of nystagmus or torsion, latency, duration of nystagmus or torsion and direction of torsion.

The method and system accordingly employs a machine learning model 116 to interpret one or more graph based patterns in response to one or more visual stimuli as well non-visual stimuli to detect a presence of an abnormality, the abnormality based on one of a nystagmus pattern, eye movement pattern, head movement pattern and torsion pattern.

In another embodiment, a mixed simulation is provided to the user, the mixed stimulation including real-life projections of visual stimuli as well as non-visual stimuli. Accordingly, the method and system employs a machine learning model 116 to interpret one or more graph based patterns in response to one or more visual stimuli as well non-visual stimuli to detect a presence of an abnormality, the abnormality based on one of a nystagmus pattern, eye movement pattern, head movement pattern and torsion pattern The presence of an abnormality determined by the method and system may be a vestibular condition, including, but not limited to, brain diseases, tumors, nerve palsy, concussion, Attention-deficit/hyperactivity disorder (ADHD), strokes, early Parkinson's, Multiple sclerosis and Benign Paroxysmal Positional Vertigo (BPPV). Based on the combination of visual and non-visual stimuli and the response to the visual and non-visual stimuli in the form of eye movements and head movements, automatic vestibular assessment of the user is performed.

The method and system advantageously enables an automation of interpretation of graph based patterns with high accuracy by employing CNNs as well as image processing techniques, without one or more doctors/physicians having to perform a diagnosis and interpret each graph-based pattern.

Those skilled in the art will realize that the above recognized advantages and other advantages described herein are merely exemplary and are not meant to be a complete rendering of all of the advantages of the various embodiments of the invention.

The system, as described in the invention or any of its components may be embodied in the form of a computing device. The computing device can be, for example, but not limited to, a general-purpose computer, a programmed microprocessor, a micro-controller, a peripheral integrated circuit element, and other devices or arrangements of devices, which can implement the steps that constitute the method of the invention. The computing device includes a processor, a memory, a nonvolatile data storage, a display, and a user interface.

In the foregoing specification, specific embodiments of the invention have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A headgear apparatus for performing vestibular assessment of a user, the headgear apparatus comprising:

a processor;

a memory communicatively coupled to the processor;

a display device communicatively coupled to the processor and the memory, wherein the display device is configured to display a plurality of visual stimuli to the user;

a laser source communicatively coupled to the processor and memory, wherein the laser source is configured to project a laser beam providing a head-fixated target onto an external surface or wall;

a plurality of hardware devices communicatively coupled to the processor and the memory, wherein the plurality of hardware devices is configured to provide a plurality of non-visual stimuli to the user;

a plurality of infrared cameras communicatively coupled to the processor and the memory, wherein the plurality of infrared cameras is configured to measure an eye movement of the user in response to the plurality of visual stimuli, the plurality of non-visual stimuli, and the head-fixated target; and an inertial measurement device communicatively coupled to the processor and the memory, wherein the inertial measurement device is configured to determine a head movement of the user in response to the plurality of visual stimuli, the plurality of non-visual stimuli, and the head-fixated target, wherein the inertial measurement device is further configured to differentiate between a deliberate head movement and an unintentional head movement, and wherein the plurality of infrared cameras and the inertial measurement device are configured to simultaneously measure eye movement and head movement relative to the head-fixated target;

wherein the processor is configured to:

generate one or more temporally-correlated graph-based patterns based on a combination of the eye movement and the head movement of the user; and interpret the one or more temporally-correlated graph-based patterns using a machine learning model utilizing at least one of a deep neural network (DNN) and a convolutional neural network (CNN), wherein the machine learning model is trained on labeled vestibular datasets that include VOR suppression responses to the head-fixated target to detect a presence of an abnormality selected from a torsion pattern, a nystagmus pattern, or a vestibulo-ocular reflex (VOR) pattern abnormality.

2. The headgear apparatus of claim 1, wherein the plurality of visual stimuli corresponds to one of a smooth pursuit test, saccade test, optokinetic test, gaze test or a combination.

3. The headgear apparatus of claim 1, wherein the plurality of non-visual stimuli corresponds to one of mastoid vibration, caloric, Valsalva, Hyperventilation, Vestibulo-Ocular Reflex (VOR) suppression, positional stimulus, head shaking, head thrust or head impulse.

4. The headgear apparatus of claim 1, wherein a mixed simulation of visual stimuli and non-visual stimuli is provided to the user.

5. The headgear apparatus of claim 4, wherein the mixed simulation includes a real-life projection.

6. The headgear apparatus of claim 1, wherein the vestibular assessment includes identifying a vestibular condition associated with the user, wherein the vestibular condition is one of brain diseases, nerve palsy, concussion, Attention-deficit/hyperactivity disorder (ADHD), strokes, early Parkinson's, Multiple Sclerosis or Benign Paroxysmal Positional Vertigo (BPPV).

7. The headgear apparatus of claim 1 is a pair of augmented reality goggles.

8. A method for performing vestibular analysis/assessment of a user using a headgear apparatus, the method comprising:

displaying, by one or more processors of the headgear apparatus, a plurality of visual stimuli to the user;

providing, by one or more processors of the headgear apparatus, a plurality of non-visual stimuli to the user;

projecting, by a laser source communicatively coupled to the one or more processors, a laser beam providing a head-fixated target onto an external surface or wall;

measuring, using a plurality of infrared cameras communicatively coupled to the one or more processors of the headgear apparatus, an eye movement of the user in response to the plurality of visual stimuli displayed to the user, the plurality of non-visual stimuli provided to the user, and the head-fixated target; and determining, using an inertial measurement device communicatively coupled to the one or more processors of the headgear apparatus, a head movement of the user in response to the plurality of visual stimuli, the plurality of non-visual stimuli, and the head-fixated target, wherein the inertial measurement device is further configured to differentiate between a deliberate head movement and an unintentional head movement;

and wherein the plurality of infrared cameras and the inertial measurement device are configured to simultaneously measure eye movement and head movement relative to the head-fixated target;

generating, by one or more processors of the headgear apparatus, one or more temporally-correlated graph-based patterns based a combination of the eye movement and the head movement of the user; and interpreting, by the one or more processors of the headgear apparatus, the one or more temporally-correlated graph-based patterns using a machine learning model utilizing at least one of a deep neural network (DNN) and a convolutional neural network (CNN), wherein the machine learning model is trained on labeled vestibular datasets that include VOR suppression responses to the head-fixated target to detect a presence of an abnormality selected from a torsion pattern, a nystagmus pattern, or a vestibulo-ocular reflex (VOR) pattern abnormality.

9. The method of claim 8, wherein the plurality of visual stimuli corresponds to one of a smooth pursuit test, saccadic test, optokinetic test, gaze test or a combination.

10. The method of claim 8, wherein the plurality of non-visual stimuli corresponds to one of mastoid vibration, caloric, Valsalva, Hyperventilation, Vestibulo-Ocular Reflex (VOR) suppression head shaking, head thrust head impulse or positional testing.

11. The method of claim 8, wherein a mixed simulation of visual stimuli and non-visual stimuli is provided to the user.

12. The method of claim 11, wherein the mixed simulation includes a real-life projection.

13. The method of claim 8, wherein the vestibular assessment includes identifying a vestibular condition associated with the user, wherein the vestibular condition is one of brain diseases, nerve palsy, concussion, Attention-deficit/hyperactivity disorder (ADHD), strokes, early Parkinson's, Multiple Sclerosis or Benign Paroxysmal Positional Vertigo (BPPV).

14. The method of claim 8, wherein the headgear apparatus is a pair of augmented reality goggles.

* * * * *